US00PP28514P2

(12) United States Plant Patent
Koekkoek

(10) Patent No.: US PP28,514 P2
(45) Date of Patent: Oct. 10, 2017

(54) CARNATION PLANT NAMED 'HILAMBER'

(50) Latin Name: ***Dianthus* L.**
Varietal Denomination: Hilamber

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 14/999,645

(22) Filed: Jun. 8, 2016

(51) Int. Cl.
*A01H 5/02* (2006.01)

(52) U.S. Cl.
USPC ..... Plt./280

(58) Field of Classification Search
USPC ..... Plt./280
See application file for complete search history.

*Primary Examiner* — Annette Para
(74) *Attorney, Agent, or Firm* — C. A. Whealy

(57) ABSTRACT

A new and distinct cultivar of Carnation plant named 'Hilamber', characterized by its compact, uniformly mounding and upright to broadly spreading plant habit; relatively small leaves; freely flowering habit; light yellow-colored double flowers; and good container performance.

1 Drawing Sheet

Botanical designation: *Dianthus* L.
Cultivar denomination: 'HILAMBER'.

BACKGROUND OF THE INVENTION

The present invention relates to a new and distinct cultivar of Carnation plant, botanically known as *Dianthus* L., grown commercially as a container plant and hereinafter referred to by the name 'Hilamber'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in June, 2011 of a proprietary selection of *Dianthus* L. identified as code number 1196, not patented, as the female, or seed, parent with a proprietary selection of *Dianthus* L. identified as code number A46207-05, not patented, as the male, or pollen, parent. The new Carnation plant was discovered and selected by the Inventor as a single flowering plant from within the progeny of the stated cross-pollination in a controlled greenhouse environment in De Kwakel, The Netherlands in September, 2012.

Asexual reproduction of the new Carnation plant by terminal cuttings propagated in a controlled greenhouse environment in De Kwakel, The Netherlands since October, 2012 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilamber'. These characteristics in combination distinguish 'Hilamber' as a new and distinct Carnation plant:

1. Compact, uniformly mounding and upright to broadly spreading plant habit.
2. Relatively small leaves.
3. Freely flowering habit.
4. Light yellow-colored double flowers.
5. Good container performance.

Plants of the new Carnation differ primarily from plants of the female parent selection in the following characteristics:

1. Plants of the new Carnation are more compact than plants of the female parent selection.
2. Flowers of plants of the new Carnation are more fully double than flowers of plants of the female parent selection.
3. Plants of the new Carnation and the female parent selection differ in flower color as plants of the female parent selection have pink-colored flowers.

Plants of the new Carnation differ primarily from plants of the male parent selection in the following characteristics:

1. Plants of the new Carnation have larger flowers than plants of the male parent selection.
2. Plants of the new Carnation and the male parent selection differ in flower color as plants of the male parent selection have white-colored flowers.

Plants of the new Carnation also can be compared to plants of *Dianthus* L. 'Bling Bling', not patented. In side-by-side comparisons, plants of the new Carnation differ primarily from plants of 'Bling Bling' in the following characteristics:

1. Plants of the new Carnation are more compact than plants of 'Bling Bling'.
2. Plants of the new Carnation are more freely branching than plants of 'Bling Bling'.
3. Plants of the new Carnation and 'Bling Bling' differ in flower color as plants of 'Bling Bling' have yellow and orange-colored flowers.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilamber' grown in a container.

DETAILED BOTANICAL DESCRIPTION

Plants used in the aforementioned photograph and following observations and measurements were grown during the spring in 10.5-cm containers in a glass-covered greenhouse in De Kwakel, The Netherlands and under cultural practices typical of commercial container Carnation production. During the production of the plants, day temperatures ranged from 12° C. to 17° C., night temperatures averaged 12° C. and light levels averaged 7,000 lux. Plants used for the photograph and description were twelve weeks old. In the following description, color references are made to The Royal Horticultural Society Colour Chart, 2015 Edition, except where general terms of ordinary dictionary significance are used.

Botanical classification: *Dianthus* L. 'Hilamber'.

Parentage:

*Female, or seed, parent*.—Proprietary selection of *Dianthus* L. identified as code number 1196, not patented.

*Male, or pollen, parent*.—Proprietary selection of *Dianthus* L. identified as code number A46207-05, not patented.

Propagation:

*Type*.—By terminal cuttings.

*Time to initiate roots, summer*.—About six days at temperatures ranging from 20° C. to 25° C.

*Time to initiate roots, winter*.—About eight days at temperatures about 18° C.

*Time to produce a rooted young plant, summer*.—About three weeks at temperatures ranging from 20° C. to 25° C.

*Time to produce a rooted young plant, winter*.—About five weeks at temperatures about 18° C.

*Root description*.—Medium in thickness, fibrous; whitish in color.

*Rooting habit*.—Moderate branching; medium density.

Plant description:

*Plant and growth habit*.—Herbaceous perennial, typically grown as a container plant; compact, uniformly mounding, upright to broadly spreading plant habit; moderately vigorous growth habit.

*Plant height, soil level to top of foliar plane*.—About 15 cm.

*Plant height, soil level to top of floral plane*.—About 15.4 cm.

*Plant diameter or spread*.—About 23.2 cm.

*Lateral branches*.—Branching habit: Freely branching habit with about nine main (basal) stems; each main stem with about five lateral branches; pinching enhances lateral branch development. Length: About 6.9 cm. Diameter: About 3 mm to 4 mm. Internode length: About 1.6 cm. Strength: Strong. Aspect: Upright to about 50° from vertical. Texture and luster: Smooth, glabrous, waxy cuticle; matte. Color, developing: Close to 145B; at internodes, close to 145C. Color, developed: Close to NN137A to NN137B; thin waxy cuticle, close to 188A.

Leaf description:

*Arrangement*.—Opposite, simple; sessile.

*Length*.—About 9.6 cm.

*Width*.—About 6 mm.

*Shape*.—Narrowly oblanceolate; slightly to moderately carinate.

*Apex*.—Acute.

*Base*.—Attenuate; decurrent.

*Margin*.—Entire.

*Texture and luster, upper and lower surfaces*.—Smooth, glabrous, waxy cuticle; matte.

*Venation pattern*.—Parallel.

*Color*.—Developing leaves, upper surface: Close to 143B; towards the base, close to 144B. Developing leaves, lower surface: Close to 137C; towards the base, close to 144A to 144B. Fully expanded leaves, upper surface: Close to NN137A; thin waxy cuticle, close to 189A; venation, close to NN137A. Fully expanded leaves, lower surface: Close to NN137A; thin waxy cuticle, close to 189A; venation, close to 143A.

Flower description:

*Flower form and flowering habit*.—Double flowers arranged in panicles with about eight flowers each; freely flowering habit with about 75 flowers developing during the flowering season; flowers face mostly upright to slightly outwardly.

*Natural flowering season*.—Flowering is continuous from the spring to late summer in The Netherlands; plants begin flowering about nine to eleven weeks after planting.

*Postproduction longevity*.—Flowers last about ten days on the plant; flowers not persistent.

*Fragrance*.—Moderately fragrant; clove-like, sweet.

*Flower buds*.—Length: About 2.5 cm. Diameter: About 1.2 cm. Shape: Oblong to obovate. Texture and luster: Smooth, glabrous; matte. Color: Close to 137C; towards the base, close to 145C; petal apices, close to 4B.

*Inflorescence height*.—About 8.5 cm.

*Inflorescence diameter*.—About 9.2 cm.

*Flower diameter*.—About 5 cm.

*Flower depth*.—About 3.7 cm.

*Petals*.—Quantity and arrangement: About 15 petals arranged in about three whorls. Length: About 3.9 cm. Width: About 2.2 cm. Shape: Spatulate. Apex: Praemorse. Base: Narrowly cuneate. Margin: Towards the apex, irregularly dentate; towards the base, entire; moderately undulate. Texture and luster, upper surface: Smooth, glabrous; moderately velvety; matte. Texture and luster, lower surface: Smooth, glabrous; slightly velvety; matte. Color: When opening, upper and lower surfaces: Close to 4B; towards the margins and apex, close to 5B; at the base, close to between 145D and 150D. Fully opened, upper and lower surfaces: Close to 4B; towards the margins and apex, close to 5B; margin edge, tinged with close to 20B to 20C; at the base, close to between 145D and 150D; venation, similar to lamina color; color does not change with development.

*Petaloids*.—Quantity and arrangement: About 65 petaloids arranged in about 13 whorls. Length: About 2.9 cm. Width: About 1.1 cm. Shape: Irregularly spatulate. Apex: Praemorse. Base: Narrowly cuneate. Margin: Towards the apex, irregularly dentate; towards the base, entire; moderately to strongly undulate. Texture and luster, upper surface: Smooth, glabrous; moderately velvety; matte. Texture and luster, lower surface: Smooth, glabrous; slightly velvety; matte. Color: When opening, upper and lower surfaces: Close to 4B; towards the margins and apex, close to 5B; at the base, close to between 145D and 150D. Fully opened, upper and lower surfaces: Close to 4B; towards the margins and apex, close to 5B; margin edge, tinged with close to 20B to 20C; at the base, close to between 145D and 150D; venation, similar to lamina color; color does not change with development.

*Sepals*.—Quantity and arrangement: Five sepals arranged in a single whorl; proximal 70% portion of the sepals are fused into a campanulate-shaped calyx. Calyx length: About 2 cm. Calyx diameter: About 1.9 cm. Sepal length: About 2.3 cm. Sepal width, at base of "free" portion: About 8 mm. Shape: Oblong to narrowly oblong. Apex: Acute. Margin: Entire. Texture and luster, upper surface: Smooth, glabrous; glossy. Texture and luster, lower surface: Smooth, glabrous; matte. Color: When opening, upper surface: Close to 148D; towards the apex, close to 148C. When opening, lower surface: Close to 137C; towards the base, close to 145C. Fully opened, upper surface: Close to 148D; towards the apex, close to 148C. Fully opened, lower surface: Close to 143A; towards the base, close to 144B.

*Peduncles*.—Length: About 4 cm. Diameter: About 3.5 mm. Strength: Strong. Aspect: About 25° from branch axis. Texture and luster: Smooth, glabrous; waxy; matte. Color: Close to NN137B; thin waxy layer, close to 188A.

*Pedicels*.—Length: About 1.1 cm. Diameter: About 2 mm. Strength: Moderately strong. Aspect: About 25° from the peduncle axis. Texture and luster: Smooth, glabrous, waxy; matte. Color: Close to 143A; thin waxy layer, close to 188B.

*Reproductive organs*.—Stamens: Quantity: About 20 stamens per flower; strongly deformed. Filament length: About 5 mm. Filament color: Close to 157D. Anther length: About 1 mm. Anther shape: Oblong. Anther color: Close to 161D. Pollen: None produced. Pistils: Quantity: About three per flower. Pistil length: About 2.1 cm. Stigma diameter: About 3 mm. Stigma shape: Pointed, spirally curved. Stigma color: Close to 29C to 29D. Style length: About 1.7 cm. Style color: Close to NN155D. Ovary color: Close to 144B; towards the base, close to 144C. Fruits and seeds: Fruit and seed development have not been observed on plants of the new Carnation.

Disease & pest resistance: Plants of the new Carnation have not been observed to be resistant to pathogens and pests common to Carnation plants.

Temperature tolerance: Plants of the new Carnation have been observed to tolerate high temperatures about 35° C. and to be suitable for USDA Hardiness Zones 5 to 9.

It is claimed:

1. A new and distinct Carnation plant named 'Hilamber' as illustrated and described.

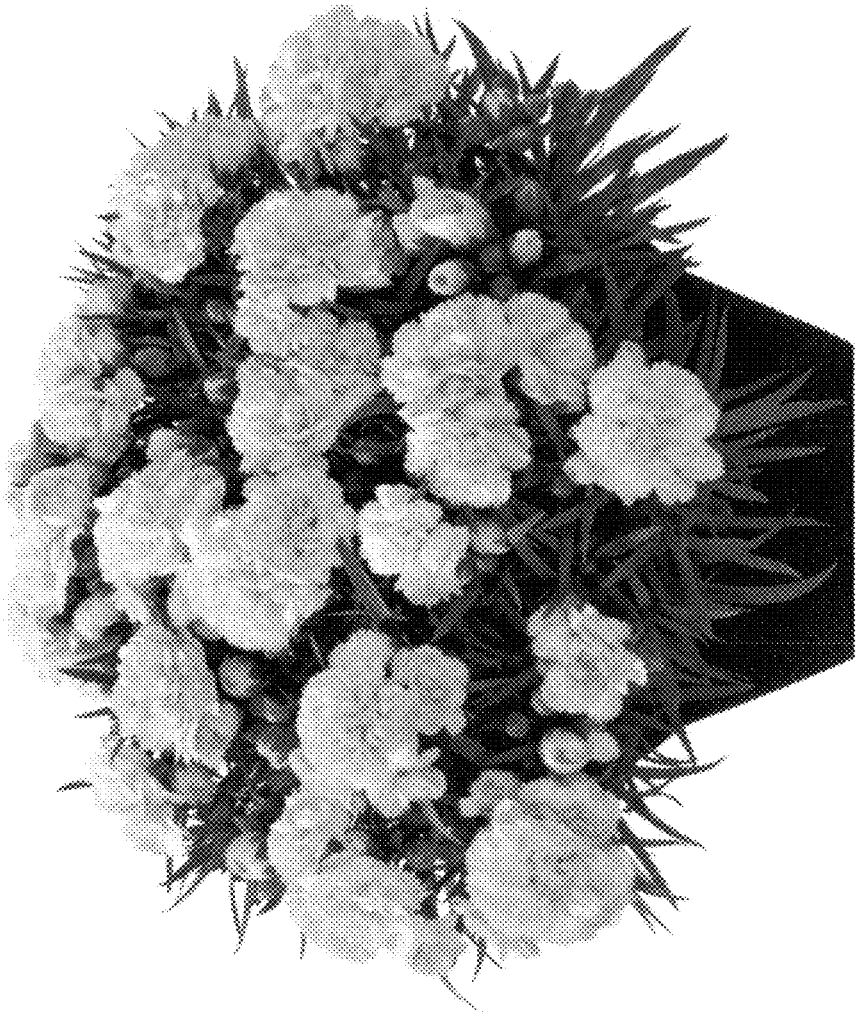

* * * * *